(12) United States Patent
Warren (10) Patent No.: US 10,022,069 B2
(45) Date of Patent: Jul. 17, 2018

(54) APPARATUS AND METHOD FOR MEASURING AN ANATOMICAL ANGLE OF A BODY

(71) Applicant: Hayley Warren, Subiaco (AU)

(72) Inventor: Hayley Warren, Subiaco (AU)

(*) Notice: Subject to any disclaimer, the term of this patent is extended or adjusted under 35 U.S.C. 154(b) by 49 days.

(21) Appl. No.: 14/790,015

(22) Filed: Jul. 2, 2015

(65) Prior Publication Data

US 2016/0174876 A1  Jun. 23, 2016

Related U.S. Application Data

(63) Continuation of application No. 13/261,037, filed as application No. PCT/AU2010/000628 on May 24, 2010.

(30) Foreign Application Priority Data

May 23, 2009  (AU) ................................ 2009100486

(51) Int. Cl.
*A61B 5/107* (2006.01)
*A61B 5/00* (2006.01)
*G01B 9/10* (2006.01)

(52) U.S. Cl.
CPC ............ *A61B 5/1071* (2013.01); *A61B 5/742* (2013.01); *G01B 9/10* (2013.01); *A61B 2560/0425* (2013.01)

(58) Field of Classification Search
CPC ................................ A61B 5/1071; G01B 9/10
USPC ..................................... 600/595; 33/511–512
See application file for complete search history.

(56) References Cited

U.S. PATENT DOCUMENTS

| | | | |
|---|---|---|---|
| 5,832,422 A | 11/1998 | Wiedenhoefer | |
| 7,293,363 B1* | 11/2007 | Parker | A61B 5/1071 33/1 N |
| 8,436,737 B1* | 5/2013 | Trout | A61B 5/1116 340/573.1 |
| 2001/0037581 A1* | 11/2001 | Akhavan-Sigari | A61B 5/1071 33/807 |
| 2003/0226268 A1* | 12/2003 | Gibson | A61B 5/1071 33/281 |
| 2005/0021044 A1* | 1/2005 | Stone | A61B 17/1778 606/102 |
| 2007/0032748 A1 | 2/2007 | McNeil et al. | |

(Continued)

FOREIGN PATENT DOCUMENTS

| CA | 2241359 | * 12/1999 | ............... G01C 1/00 |
|---|---|---|---|
| WO | 20090902000 | 7/2009 | |

OTHER PUBLICATIONS

Caruso "Application of Magnetic Sensors for Low Cost Compass Systems" 2000 IEEE.*

*Primary Examiner* — Michael C Stout
(74) *Attorney, Agent, or Firm* — Mark M. Friedman (57) ABSTRACT

An apparatus (20) for automatically measuring an anatomical angle of a body, the apparatus (20) comprising aligning means (23) for aligning an axis (22) of the apparatus (20) with anatomical landmarks of the body, sensing means (30) for sensing an orientation of the axis (22) while the axis is aligned with the landmarks, and processing means (40) for processing the sensed orientation. The sensing means (30) comprises a magnetometer (32) and an accelerometer (31), and the aligning means comprises a pair of lasers.

18 Claims, 10 Drawing Sheets

(56) References Cited

U.S. PATENT DOCUMENTS

| | | | |
|---|---|---|---|
| 2008/0221485 A1* | 9/2008 | Lissek | A61B 5/103 600/595 |
| 2009/0038168 A1* | 2/2009 | Wixey | B43L 7/10 33/471 |
| 2010/0063508 A1* | 3/2010 | Borja | A61B 17/157 606/88 |
| 2011/0213275 A1* | 9/2011 | Boos | A61B 5/1071 600/595 |

* cited by examiner

APPARATUS AND METHOD FOR MEASURING AN ANATOMICAL ANGLE OF A BODY

FIELD OF THE INVENTION

The present invention relates generally to an apparatus and method for measuring an anatomical angle of a body.

Although the present invention will be described with particular reference to measuring an anatomical angle of a human body, it will nevertheless be appreciated that the invention is not necessarily limited to this use.

BACKGROUND ART

Goniometers are apparatus which are used by physiotherapists and the like to measure anatomical angles of a body. For example, they are often used to measure the range of angular motion of joints.

The following patent documents disclose examples of known goniometers as well as other apparatus for measuring angles: U.S. Pat. No. 4,771,548 (Donnery), United States Patent Application Publication No. 2006/0137201 A1 (Dixon, et al.), U.S. Pat. No. 6,469,666 (Tonn), U.S. Pat. No. 7,337,751 (Lopez, et al.), U.S. Pat. No. 4,442,606 (Graham, et al.), U.S. Pat. No. 7,204,030 (Kattar), U.S. Pat. No. 7,293,363 (Emmett L. Parker), United States Patent Application Publication No. 2007/0266579 A1 (Briscoe, at al.), U.S. Pat. No. 5,163,228 (Edwards, et al.), U.S. Pat. No. 4,665,928 (Linial, et al.), U.S. Pat. No. 3,879,136 (Takeda), U.S. Pat. No. 4,665,928 (Linial, et al.), United States Patent Application Publication No. 2003/0226268 A1 (Gibson), U.S. Pat. No. 7,359,750 (Song, et al.), U.S. Pat. No. 5,253,655 (Stone, et al.), and International Patent Application No. PCT/DE1993/000891.

Many existing goniometers include a pair of aligning arms which are able to pivot relative to each other. In use, each arm is aligned with anatomical landmarks which are adjacent to the body part whose angle is being measured. For example, if a goniometer with arms is used to measure the angle between the upper part of a person's leg and the lower part of their leg, one of the arms of the goniometer will be aligned with landmarks on the upper part of the leg while the other arm is aligned with landmarks on the lower part of the leg. Once the arms have been properly aligned with the upper and lower leg parts, the angle between the arms corresponds to the angle between the leg parts and can be read off an analogue scale of the goniometer.

Goniometers of the above-described type suffer from the disadvantage that the arms are often not long enough to accurately align them with some anatomical landmarks. When this situation arises, the person using the goniometer will usually use an eye-balling approach to align the arms with the landmarks as best they can. The accuracy of the measurement which is obtained will be reduced if the arms are not properly aligned with the landmarks.

Although this problem can be overcome by extending the length of the arms (e.g. by making the arms extendable) so that they are able to reach all of the landmarks that they need to be aligned with when making a measurement, doing so would make the arms somewhat of an obstruction to a user and also make them more vulnerable to being broken or bent.

Measurement inaccuracy can also be introduced by the analogue scale of the goniometer from which the angle measurement is read. This is because the user needs to interpret the reading from the scale. Although some devices include a digital display which can address this problem, the displays tend to be small and difficult to read.

For various reasons, including those given above, many existing goniometers have poor inter therapist reliability because the variability of readings from one user to another tends to be significant. For example, there can be a 5-10 degree variance between different users. Similarly, many existing goniometers have poor intra therapist reliability because the variability of readings from the same user tends to be significant. As a consequence, measurements obtained from such goniometers are generally not taken seriously.

The inaccuracy and variance of readings obtained from existing goniometers can have significant negative consequences. For example, if a post-operative patient who has had a joint operated on must gain a certain amount of range of motion in that joint before they are able to be discharged from hospital, and if a therapist uses a goniometer to measure the range of motion of the joint to determine whether or not the patient has gained the required amount of motion, the date on which the patient is discharged will be unnecessarily delayed if the patient does have the required range of motion but, due to an inaccurate measurement obtained from the goniometer, the measured range indicates that they do not have the required range. An unnecessary delay in the patient being discharged means that the patient will needlessly be occupying a hospital bed which should be made available to someone else.

Another problem with many existing goniometers is that a user often needs to operate them with both of their hands. This means that while they are performing a measurement with such a device they do not have a hand available to assist the person on whom they are performing the measurement, or to write down the measurement which is obtained from the device.

Furthermore, many existing goniometers (particularly those which have aligning arms) are quite bulky. This bulkiness can contribute to the need for users to operate them with both hands.

Existing goniometers which have short aligning arms and/or analogue scales can also be time-consuming to use, particularly if an accurate measurement is required. This is because it can take time to properly align the arms with landmarks that the arms cannot reach, and because it can take time to properly read the scale.

In addition, at present, different sized goniometers are required to obtain measurements of different sized joints. A large goniometer is required in order to take measurements for the hip and other large joints. A small goniometer is required in order to take measurements of medium size joints and also to take measurements on the pediatric population. A finger joint goniometer is required in order to measure the angle of finger joints.

It is against this background that the present invention has been developed.

SUMMARY OF THE INVENTION

It is an object of the present invention to overcome, or at least ameliorate, one or more of the deficiencies of the prior art mentioned above, or to provide the consumer with a useful or commercial choice.

Other objects and advantages of the present invention will become apparent from the following description, taken in connection with the accompanying drawings, wherein, by way of illustration and example, a preferred embodiment of the present invention is disclosed.

According to a first broad aspect of the present invention, there is provided an apparatus for measuring an anatomical angle of a body, the apparatus comprising aligning means for aligning an axis of the apparatus with anatomical landmarks of the body, sensing means for sensing an orientation of the axis while the axis is aligned with the landmarks, and processing means for processing the sensed orientation.

In one preferred embodiment, the processing means is able to process a sensed first orientation of the axis and a sensed second orientation of the axis to determine an angle between the axis in the sensed first orientation and the axis in the sensed second orientation. Preferably, the apparatus also comprises another aligning means for aligning the axis with anatomical landmarks of the body. Preferably, the sensing means includes a tilt sensor for sensing the tilt of the axis, and a magnetic sensor for sensing the direction of the axis relative to a magnetic field. Preferably, the tilt sensor is able to sense the pitch and roll of the axis. It is preferred that the tilt sensor is an accelerometer. It is also preferred that the magnetic sensor is a magnetometer.

In another preferred embodiment, the apparatus also comprises another aligning means for aligning another axis of the apparatus with other anatomical landmarks of the body, the aligning means are able to be pivoted relative to each other so as to vary an angle between the axes, and the processing means is able to process the sensed orientation to determine the angle between the axes.

Preferably, each aligning means is a light source. It is preferred that the light source is a focused or collimated light source. It is particularly preferred that the light source is a laser. For example, the laser may be a solid-state laser.

Preferably, the processing means is a microprocessor.

Preferably, the apparatus also comprises a display for displaying the measured angle. It is preferred that the display is a liquid-crystal display (LCD). It is also preferred that the measured angle is displayed in units of degrees.

Preferably, the apparatus also comprises at least one switch for allowing a user to control the operation of the apparatus. It is preferred that the switch is a pushbutton switch.

Preferably, the apparatus also comprises storage means for storing instructions or data for processing by the processing means. It is preferred that the storage means is a non-volatile memory.

Preferably, the apparatus is able to be powered by a battery. It is preferred that the apparatus is able to be powered by a lithium battery.

It is preferred that the apparatus also comprises a charger for charging the battery. The charger is preferably a Universal Serial Bus (USB) charger.

Preferably, the apparatus also comprises a housing for housing the aligning means, sensing means and processing means.

According to a second broad aspect of the present invention, there is provided a method for measuring an anatomical angle of a body, the method comprising the steps of:
 aligning an axis with anatomical landmarks of the body;
 sensing an orientation of the axis while the axis is aligned with the landmarks; and
 processing the sensed orientation.

In one preferred embodiment, the sensing step includes sensing a first orientation of the axis and sensing a second orientation of the axis, and the processing step includes processing the first sensed orientation and the second sensed orientation to determine an angle between the axis in the sensed first orientation and the axis in the sensed second orientation. Preferably, each orientation is sensed by sensing the tilt of the axis and the direction of the axis relative to a magnetic field. It is preferred that the tilt of the axis is sensed by sensing the pitch and roll of the axis.

In another preferred embodiment, the method also comprises the step of aligning another axis with other anatomical landmarks of the body by varying an angle between the axes, and the processing step includes processing the sensed orientation to determine the angle between the axes.

Preferably, each aligning step includes aligning a light beam with the landmarks. It is preferred that the light beam is a collimated light beam. It is particularly preferred that the light beam is a laser beam.

Preferably, the method also comprises the step of displaying the measured angle.

BRIEF DESCRIPTION OF THE DRAWINGS

In order that the invention may be more fully understood and put into practice, a preferred embodiment thereof will now be described with reference to the accompanying drawings, in which.

BEST MODE(S) FOR CARRYING OUT THE INVENTION

In the figures, like features of the described preferred embodiments of the present invention have been referenced with like reference numerals.

Referring to FIGS. 1 to 4, there is depicted an apparatus 20 according to a first preferred embodiment of the present invention. Apparatus 20 is for measuring an anatomical angle of a body such as a human body. Apparatus which are used for this purpose are usually referred to as goniometers by physiotherapists and the like.

Apparatus 20 includes a pair of aligning or alignment means that are each in the form of a solid-state laser 23. Lasers 23, which are diametrically opposite each other, are for aligning an axis 22 of the apparatus 20 with anatomical landmarks of a body. Each Laser 23 is able to emit a respective focused or collimated light beam in the form of a laser beam. The lasers 23 emit the laser beams outwardly from the apparatus 20 such that the laser beams are co-linear with each other and the axis 22 of the apparatus 20. Lasers 23 are preferably low-power lasers so that they do not pose a health risk.

Figure 1:
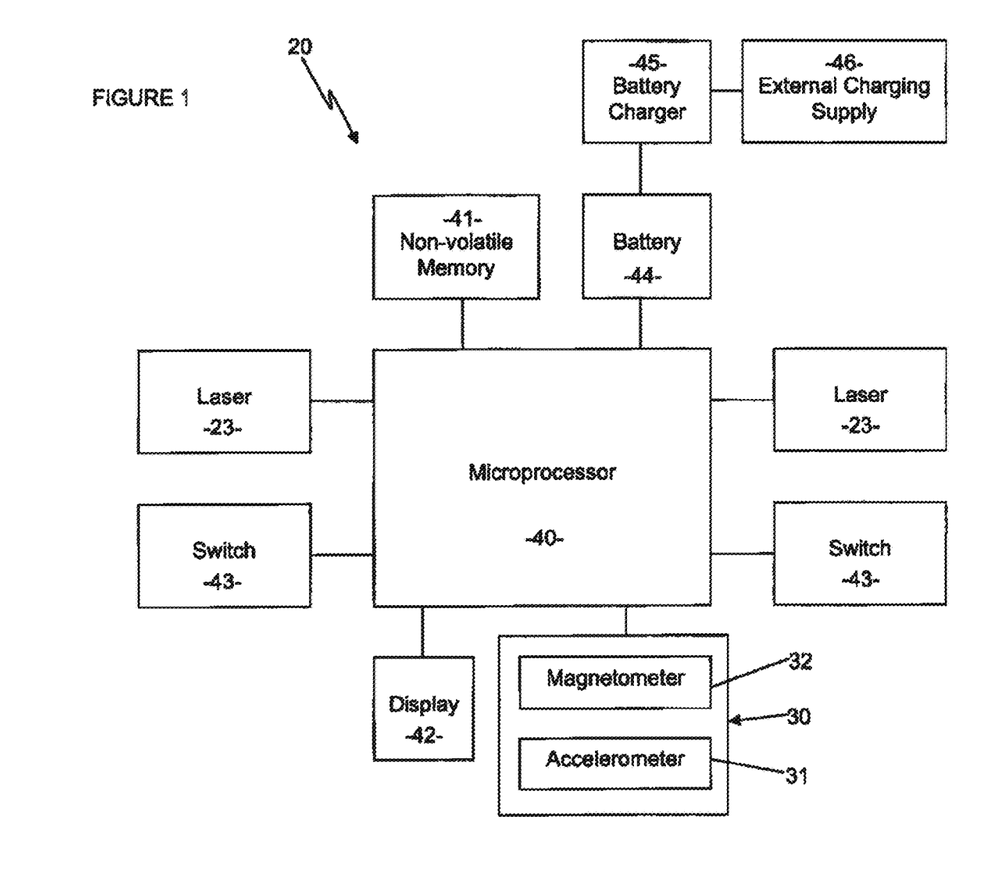
FIG. 1 is a schematic block diagram of an apparatus according to a first preferred embodiment of the present invention when a battery for powering the apparatus is being charged from an external supply of electricity.

A sensing means 30 of the apparatus 20 is a three-dimensional orientation sensor which is able to sense a first orientation of the apparatus 20 and, hence, the axis 22 in three dimensions, while the axis 22 is aligned with first anatomical landmarks of the body, and is also able to sense a second orientation of the apparatus 20 and, hence, the axis 22 in three dimensions, while the axis 22 is aligned with second anatomical landmarks of the body. Sensing means 30 includes a tilt sensor which is in the form of an accelerometer 31, and a magnetic sensor which is in the form of a magnetometer 32. Sensing means 30 is able to provide stable measurement/sensing of the three-dimensional orientation of an object in space, regardless of the object's orientation.

Accelerometer 31 is able to sense the tilt of the apparatus 20 and, hence, the axis 22. In particular, accelerometer 31 is able to sense the pitch (i.e. up/down position) and roll (i.e. side to side rocking position) of the apparatus 20 and, hence, the axis 22.

Magnetometer 32 is able to sense the yaw (rotational position about a vertical axis) of the apparatus 20 and, hence, the axis 22 relative to a magnetic field such as the earth's magnetic field.

The three-dimensional orientation of the apparatus 20 and axis 22, including the pitch, roll and yaw of the apparatus 20 and axis 22, which is sensed by the sensing means 30 is able to be output by the sensing means 30 to a processing means which is in the form of a microprocessor 40. The sensed three-dimensional orientation is output by the sensing means 30 in the form of three-dimensional coordinates. In addition to the accelerometer 31 and magnetometer 32, sensing means 30 includes interfacing circuitry (not depicted) for interfacing the accelerometer 31 and the magnetometer 32 with the microprocessor. Microprocessor 40 is able to determine an angle between the axis 22 in the sensed first orientation and the axis 22 in the sensed second orientation by processing the output of the sensing means 30 in accordance with computer-readable instructions which are able to be read by the microprocessor 40 and which are stored on storage means which is in the form of a non-volatile memory 41. Microprocessor 40 is able to output the determined angle to a liquid-crystal display (LCD) 42 which is then able to display the angle numerically in units of degrees. LCD 42 has a height of 3241 mm, and a width of 61.82 mm.

Suitably pressing a pair of pushbutton switches 43 enables a user to control the operation of the microprocessor 40 and, hence, the apparatus 20.

Apparatus 20 is powered by a battery 44. The battery 44 may for example be a long-life lithium battery. The battery 44 can be charged by a battery charger such as a Universal Serial Bus (USB) charger 45 which is connected to an external charging supply of electricity 46.

Lasers 23, sensing means 30 including the accelerometer 31 and magnetometer 32, microprocessor 40, non-volatile memory 41, LCD 42, and switches 43 are all mounted on a printed circuit board (PCB) 47. PCB 47 is generally circular and has a radius of curvature of 30 mm. PCB 47 includes a pair of diametrically opposite recesses 48 for receiving the lasers 23. A respective pair of contact prongs 49 is secured to the PCB 47 and extends into each recess 48 from the PCB 47. Each pair of contact prongs 49 plugs into a respective slot (not depicted) in a socket (not depicted) of each laser 23.

Figure 2:
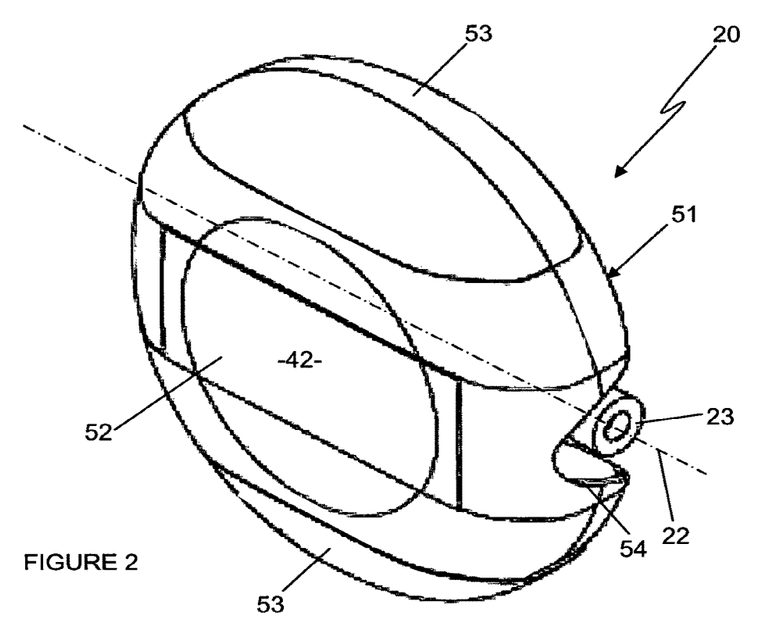
FIG. 2 is a front perspective view of the apparatus according to the first preferred embodiment of the present invention.
Figure 3:
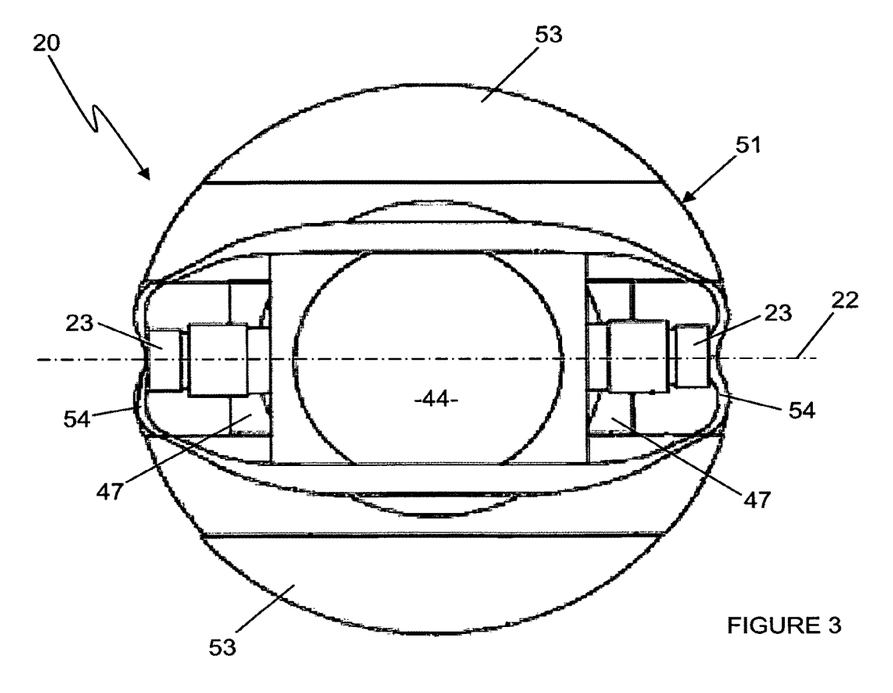
FIG. 3 is a rear elevation of the apparatus illustrated in FIG. 2.

PCB 47 is housed within a hollow disc-shaped housing 51. Housing 51 includes an opening or window 52 through which the measured angle which is displayed by LCD 42 can be viewed. It also includes a pair of buttons 53 which are located on diametrically opposite sides of the housing 51. Each button 53 operatively engages with a respective switch 43 such that the switch 43 is able to be operated by pressing the button 53. Each laser 23 is located in the housing 51 such that the lasers 23 do not protrude from the housing 51. Also, each laser 23 is located adjacent to a respective recess 54 in the housing 51 such that the housing 51 does not obstruct the laser beams which are emitted by the lasers 23.

Figure 4:
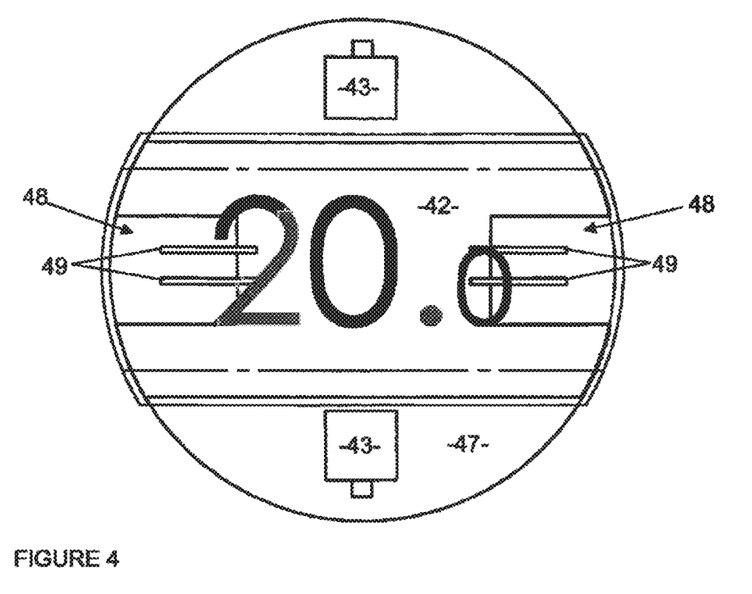
FIG. 4 depicts the printed circuit board and display of the apparatus illustrated in FIG. 2 after pressing both switches of the apparatus.

With reference to FIGS. 4 to 7, and FIG. 8 which depicts a flowchart of a method 60 of operating the apparatus 20, the apparatus 20 may be used to measure an anatomical angle of a body joint by firstly performing an activation step 61. The activation step 61 involves a user pressing both buttons 53 simultaneously with to activate (i.e. turn on) the apparatus 20. Once the buttons 53 have been pressed, both of the lasers 23 emit a laser beam, and the LCD 42 displays a numeric value in the range of 0-180 degrees. The value which is displayed by the LCD 42 depends on the orientation of the apparatus 20 and axis 22 at the time, and will change dynamically in response to a change in the orientation of the apparatus 20 and axis 22. FIG. 4 depicts the LCD 42 displaying a value of 20.0 degrees shortly after activation of the apparatus 20.

Figure 8:
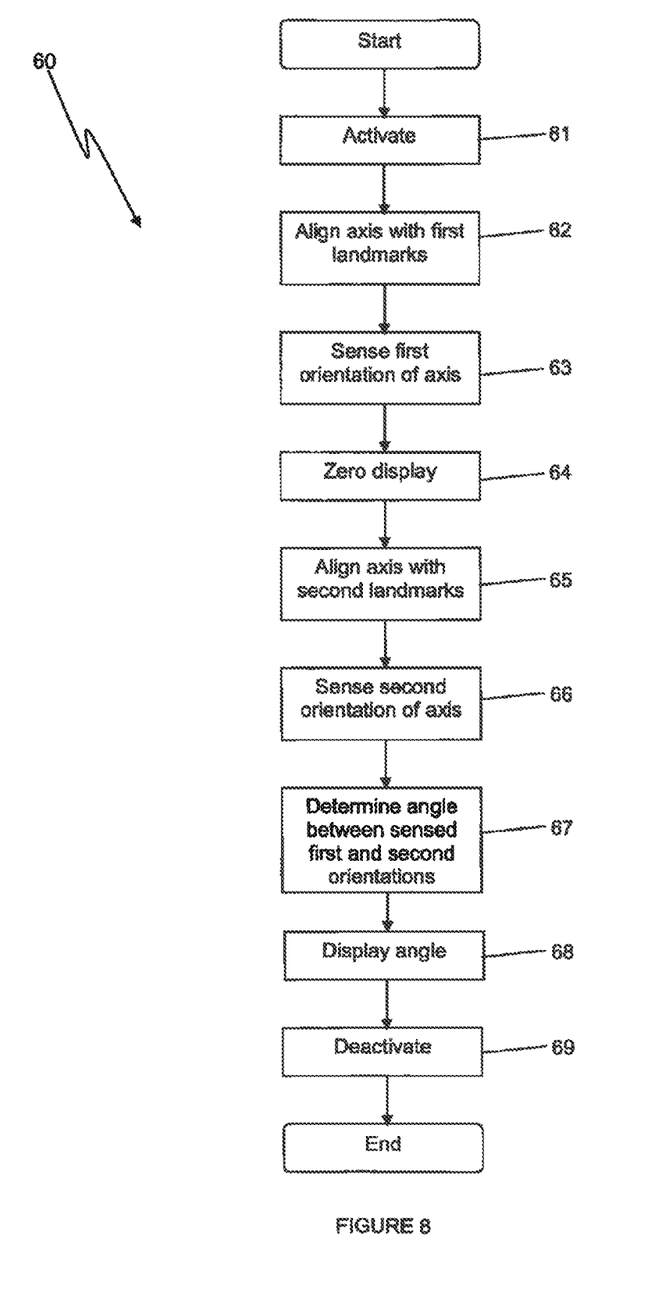
FIG. 8 is a flowchart of a method of operating the apparatus illustrated in FIGS. 1 to 7.

The next step of the method 60 is step 62 which is to align the laser beams which are emitted by the lasers 23 with first anatomical landmarks of the body which the joint forms part of. The laser beams are aligned with the first anatomical landmarks such that each laser beam intersects a respective one of the first anatomical landmarks. If the apparatus 20 is being used to measure a range of angular motion of a joint of a limb, the laser beams are initially aligned with landmarks at a distal end or part of the limb i.e. below the joint. For example, when measuring shoulder flexion when the patient is in supine, the apparatus 20 is positioned so that the laser beams align with the landmarks of the greater trochanter of the hip, along the line of the trunk to the mid axilla.

The landmarks which the laser beams are aligned with may be non joint landmarks and/or joint landmarks (e.g. landmarks indicating the axis of a joint). The particular landmarks which are used by physiotherapists and the like to measure anatomical angles are well-known in the art and will not be described at length here.

Step 63, which follows step 62, involves sensing a first orientation of the apparatus 20 and axis 22 with the sensing means 30, and then capturing that information with the microprocessor 40. The first orientation of the apparatus 20 and axis 22 is the orientation that the apparatus 20 and axis 22 have when the laser beams emitted by the lasers 23 are aligned with the first anatomical landmarks of the body. Pressing both buttons 53 simultaneously while the laser beams emitted by the lasers 23 are aligned with the first anatomical landmarks causes the first orientation which is sensed by the sensing means 30 to be captured by the microprocessor 40.

Figure 5:
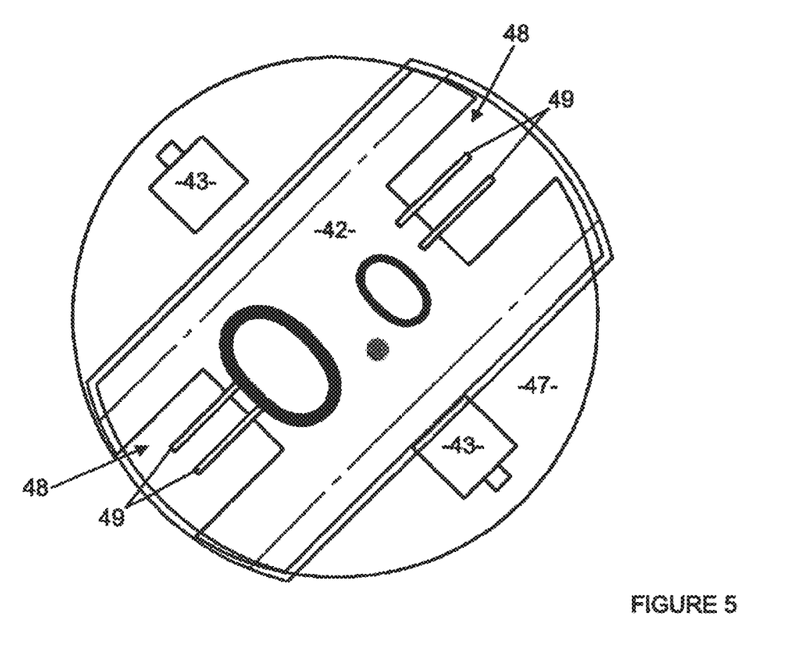
FIG. 5 depicts the printed circuit board and display after both switches are pressed again.

Following step 63, the apparatus 20 automatically performs step 64 which is to zero the numeric value which is displayed by the LCD 42 so that the LCD will display a value of 0.0 degrees while the apparatus 20 and axis 22 are in the first orientation. FIG. 5 depicts the LCD 42 displaying a value of 0.0 degrees after the first orientation of the apparatus 20 and axis 22 have been detected, and after the numeric value displayed by the LCD 42 has been zeroed.

In other embodiments, the numeric value which is displayed by the LCD 42 may be set to zero at the time that the apparatus 20 is activated.

The next step of the method 60 is step 65 which is to align the laser beams which are emitted by the lasers 23 with second anatomical landmarks of the body which the joint forms part of. The laser beams are aligned with the second anatomical landmarks such that each laser beam intersects a respective one of the second anatomical landmarks. If the apparatus 20 is being used to measure a range of angular motion of a joint of a limb, the laser beams are aligned with landmarks at a proximal end or part of the limb (i.e. above the joint) after movement of the joint. For example, when measuring shoulder flexion, the apparatus 20 is positioned so that the laser beams align with the landmarks of the mid axilla to the medial epicondyle on the humerus.

Step 66, which follows step 63 involves sensing a second orientation of the apparatus 20 and axis 22, and capturing that information. The second orientation of the apparatus 20 and axis 22 is the orientation that the apparatus 20 and axis 22 have when the laser beams emitted by the lasers 23 are aligned with the second anatomical landmarks of the body. Pressing both buttons simultaneously while the laser beams emitted by the lasers 23 are aligned with the second anatomical landmarks causes the second orientation to be captured from the sensing means 30 by the microprocessor 40.

Step 67 of the method 60 occurs automatically after step 66. In step 67, the microprocessor 40 processes the sensed first orientation and the sensed second orientation to determine what the measured anatomical angle of the joint is.

The sensed first orientation includes a vector A (i.e. Axyz) which is an initial reference position. Vector A is sensed by the magnetometer 32, and includes pitch and roll angles which are sensed by the accelerometer 31. The sensed second orientation includes a vector B (i.e. Bxyz) which is a final reference position. Vector B is sensed by the magnetometer 32, and includes pitch and roll angles for vector B which are sensed by the accelerometer 31. Microprocessor 40 processes the sensed first orientation and the sensed second orientation by transposing vector A and Vector B to the horizontal plane so that vector A (i.e. Axyz) becomes vector A'xy, and so that vector B (i.e. Bxyz) becomes vector B'xy. The microprocessor 40 then determines the angle between transposed vector A'xy and transposed vector B'xy, and this is the angle which is displayed by the LCD 42 at step 68. A similar method is used by a compass system disclosed in a published article which is entitled "Applications of Magnetic Sensors for Low Cost Compass Systems", by Michel J. Caruso of Honeywell, SSEC, and which is incorporated herein it its entirety by reference.

Figure 6:
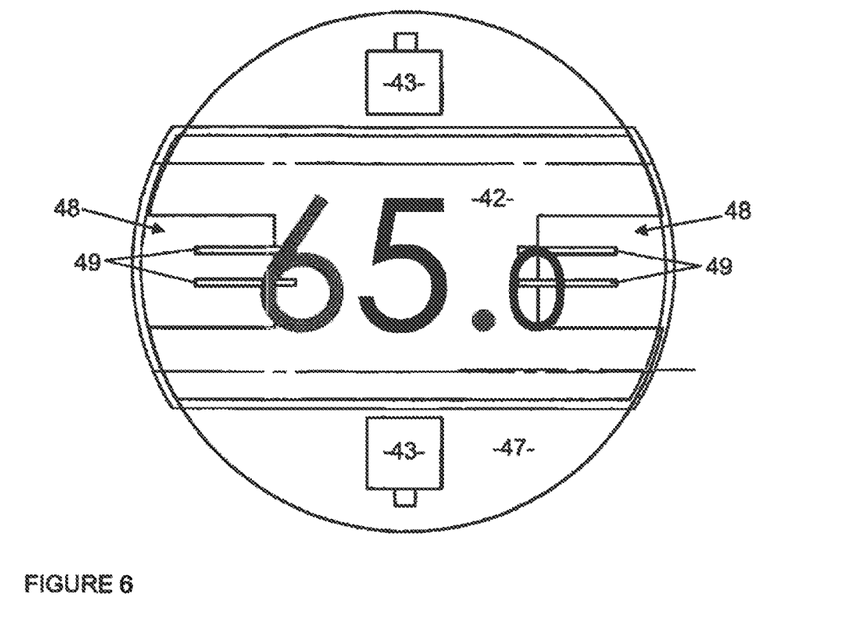
FIG. 6 depicts the printed circuit board and display after rotating the apparatus and then pressing both switches again.

After determining the anatomical angle of the joint, the next step which is performed is step 68 which involves the microprocessor 40 controlling the LCD 42 to display this information numerically and in units of degrees. The measured anatomical angle is displayed to an accuracy of a single decimal place. This information remains display by the LCD 42 irrespective of whether or not the apparatus 20 is subsequently moved. In addition, the lasers 23 are turned off so that they no longer emit laser beams. FIG. 6 depicts the LCD 42 displaying a measured angle of 65.0 degrees.

Figure 7:
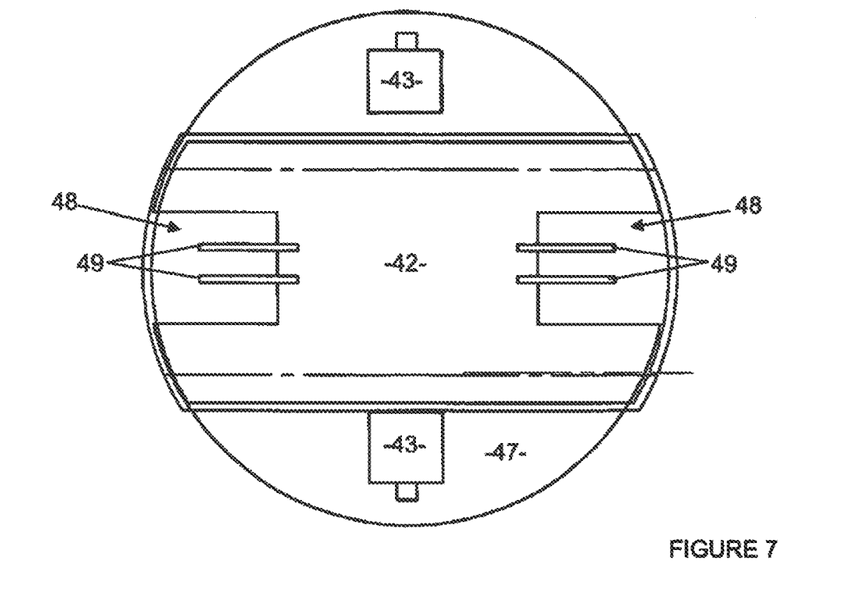
FIG. 7 depicts the printed circuit board and display after again pressing both switches.

The next step in the method is step 69 which involves the user pressing both buttons 53 so that the apparatus 20 is deactivated (i.e. turned off). FIG. 7 depicts the blank display 42 of the apparatus 20 after it has been turned off.

It will be appreciated that the sensing means 30 is not limited to including the accelerometer 31 and magnetometer 32 to sense the orientation of the axis 22 in three-dimensions, and that the sensing means 30 could use other devices/instruments to sense the three-dimensional orientation of the axis 22. For example, the sensing means 30 could use electrolytic (fluid) based tilt sensors, gimbaled mechanical structures, gyroscopes, magnetic compasses to sense the orientation of the axis 22.

The apparatus 20 may be used to measure the anatomical angle of small joints (e.g. finger joints) or the small joints of infants and the like in pediatric settings by selecting a small joint mode of operation of the apparatus by suitably pressing the buttons 53. In the small joint mode, only one of the lasers 23 is activated.

Figure 9:
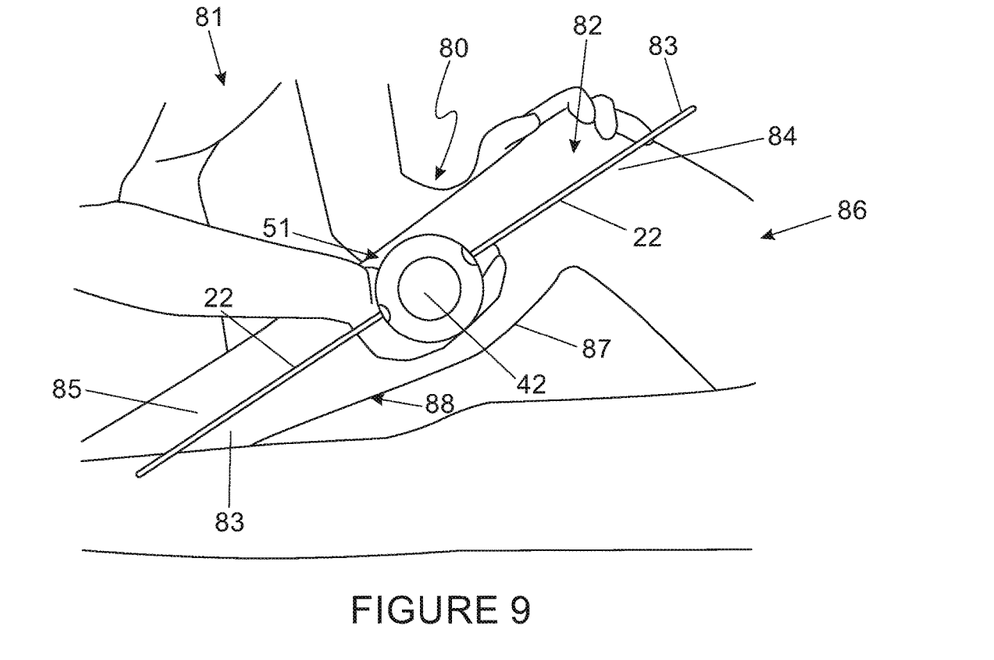
FIG. 9 depicts an apparatus according to a second preferred embodiment of the present invention being used to measure an anatomical angle at a person's knee joint.

Referring to FIG. 9, an apparatus 80 according to a second preferred embodiment of the present invention is being used by a user 81 to measure an anatomical angle of a patient's right knee joint 82. Apart from some minor cosmetic differences, apparatus 80 is identical to the apparatus 20. User 81 is shown aligning laser beams 83 which are emitted by the lasers (not depicted) of the apparatus 80 with anatomical landmarks 84, 85 of the patient's right leg 86 while holding the apparatus 80 in their right hand 87 adjacent to the patient's lower right leg 88. The apparatus 80 is initially placed on the anatomical bone of the lower right leg 88 to allow intersection of the laser beams 83 with the knee joint 82 and the proximal landmark 84 of the knee 82. Laser beams 83 are co-linear with an axis 22 of the apparatus 80.

Figure 10:
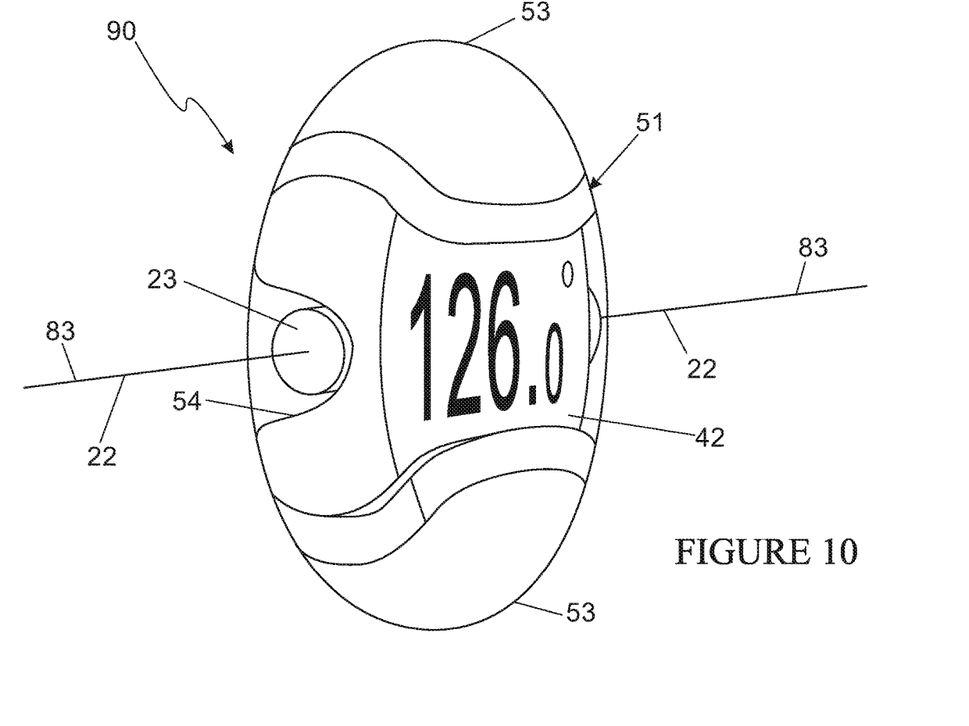
FIG. 10 depicts an apparatus according to a third preferred embodiment of the present invention when the lasers of the apparatus are activated.

FIG. 10 depicts an apparatus 90 according to a third preferred embodiment of the present invention which is also identical to the apparatus 20 apart from some minor cosmetic differences. The lasers 23 of the apparatus 90 are shown emitting laser beams 83, and the LCD 42 of the apparatus 90 is shown displaying an angular reading of 126.0 degrees. A degrees symbol '*' is displayed on the LCD 42 at the right-side of the angular reading to make it clear to a person reading the LCD 42 that the angular reading displayed thereon is in units of degrees. Laser beams 83 are co-linear with an axis 22 of the apparatus 90.

Figure 11:
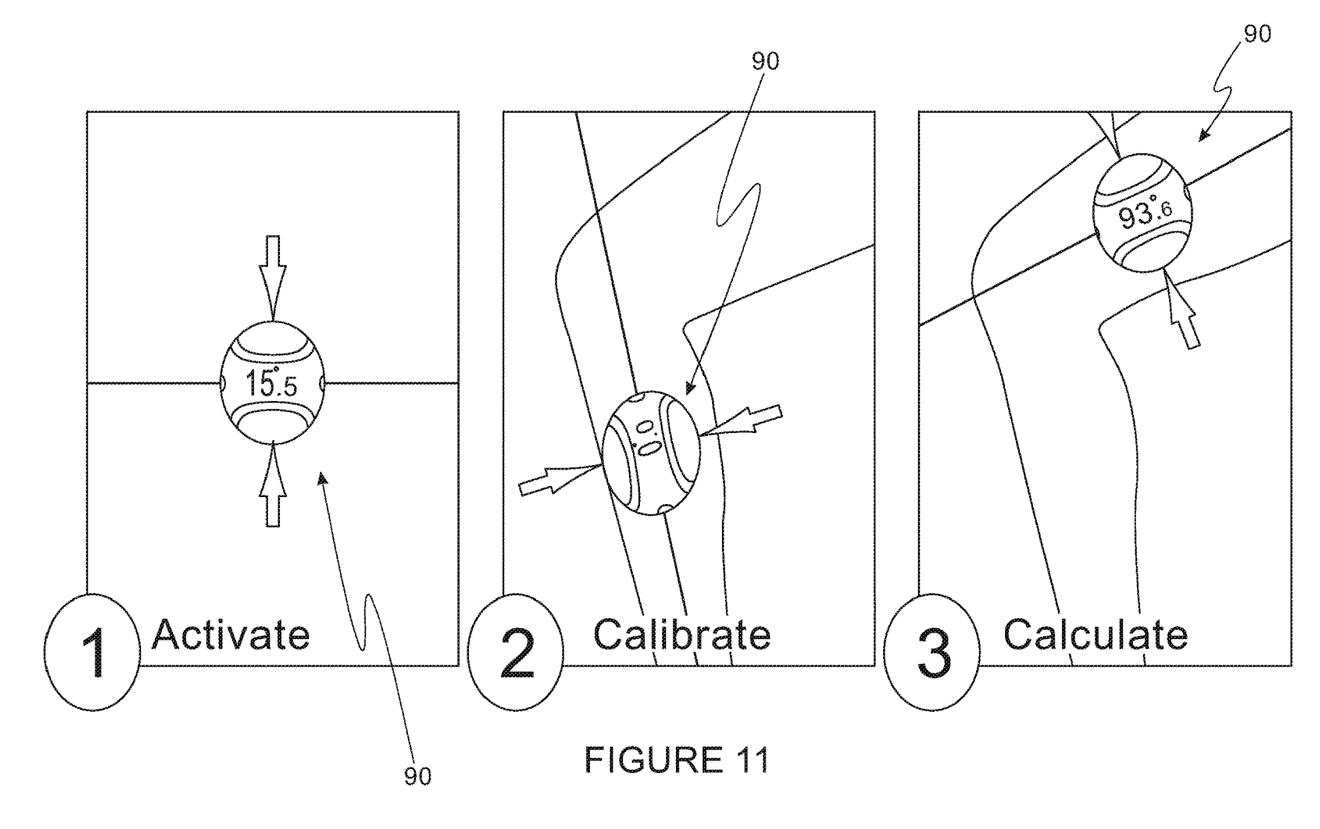
FIG. 11 depicts the three main steps in operating the apparatus illustrated in FIG. 10 to measure an anatomical angle at a person's knee joint.

FIG. 11 depicts the three main steps in operating the apparatus 90 to measure an anatomical angle at a person's knee joint. Those steps are:
 1. Activate;
 2. Calibrate; and
 3. Calculate.

In the Activate step, the apparatus 90 is activated (i.e. turned on) by pressing the buttons 53. When the apparatus 90 is activated, the LCD 42 and the lasers 23 are activated.

In the Calibrate step, the laser beams 83 are aligned with landmarks of the lower part of the leg, and then buttons 53 are pressed again to zero the reading which is displayed by the LCD 42.

In the Calculate step, the laser beams 83 are aligned with landmarks of the upper part of the leg, and then buttons 53 are pressed again so that the apparatus 90 calculates the angle between the laser beams 83 when they are aligned with the landmarks of the lower part of the leg and the laser beams 83 when they are aligned with the landmarks of the upper part of the leg.

If a user holds down the two buttons 53 for at least 5 seconds, a menu (not depicted) is displayed by the LCD 42. The menu includes a heading "Instructions for application 1, 2, 3 use", and includes the following items:

1. Landmark review
2. Small joint mode

The menu items can be scrolled through by pressing the buttons 53. To scroll up through the menu items, the topmost button 53 is pressed. To scroll down through the menu items, the bottommost button 53 is pressed. To select a menu item, the both buttons 53 are held down for at least 5 seconds.

Selecting menu item 1—Landmark review causes a submenu to be displayed by the LCD 42. The submenu includes a list of joints (e.g. shoulder, elbow, wrist, etc.) which can be measured and whose angular measurements can be reviewed.

Selecting menu item 2—Small joint mode results in only one of the lasers 23 being activated. This means that the lasers 23 can work independently of each other. Small joint mode is used when measuring an anatomical angle of a small joint. When measuring an anatomical angle of a small joint (e.g. a finger joint), both lasers 23 are unable to be used in the manner described previously because the apparatus 90 is too large and would cover the landmarks which the laser beams 83 need to be aligned with. In the small joint mode, only one of the lasers 23 is activated, and the laser beam 83 which it emits is aligned with the landmarks.

Figure 12:
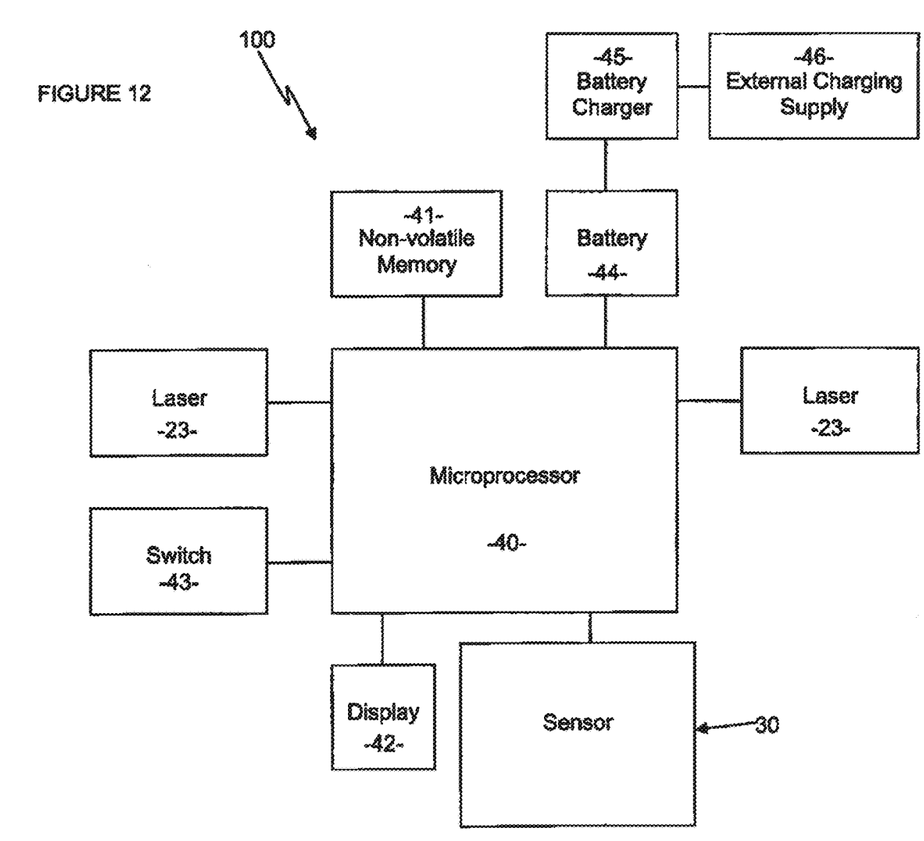
FIG. 12 is a schematic block diagram of an apparatus according to a fourth preferred embodiment of the present invention.
Figure 13A:
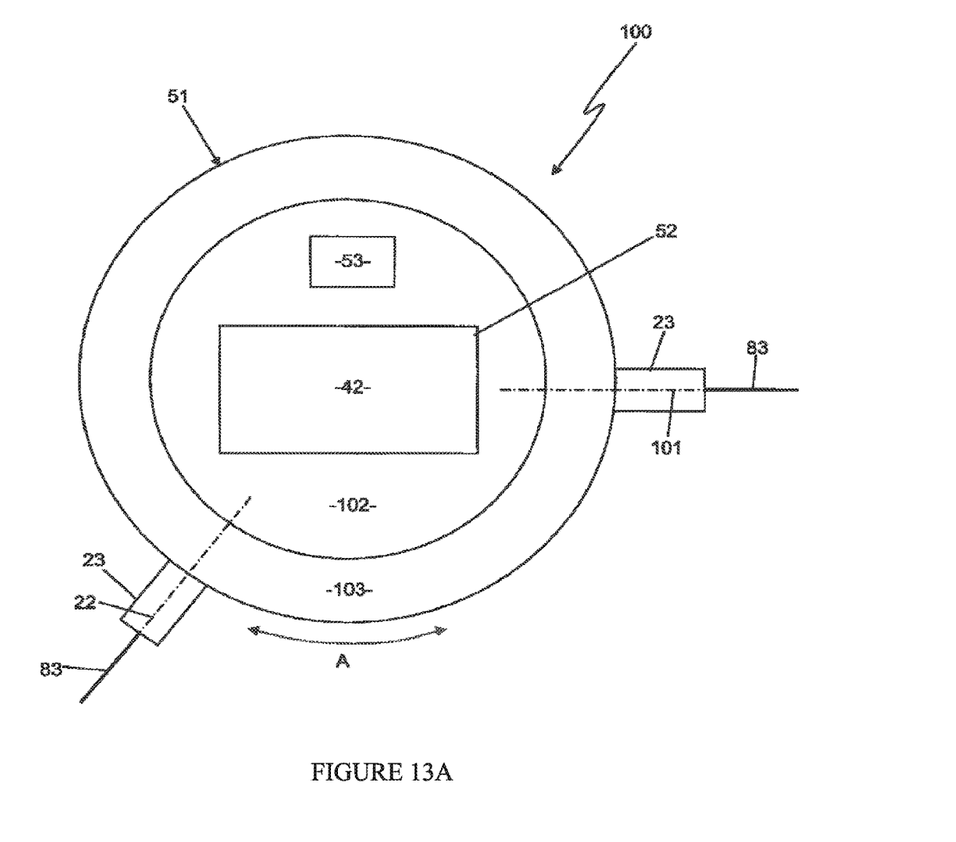
FIG. 13A is a front elevation of the apparatus according to the fourth preferred embodiment of the present invention.

Referring to FIGS. 12 and 13, there is depicted an apparatus 100 according to a fourth preferred embodiment of the present invention. Apparatus 100 is for measuring an anatomical angle of a body such as a human body. Apparatus which are used for this purpose are usually referred to as goniometers by physiotherapists and the like.

Apparatus 100 includes an aligning or alignment means that are each in the form of a solid-state laser 23. Lasers 23 are for aligning a first axis 101 of the apparatus 100 with first anatomical landmarks of a human body, and for aligning a second axis 22 of the apparatus 100 with second anatomical landmarks of the body. Lasers 23 are each able to emit a respective focused or collimated light beam in the form of a laser beam 83. The lasers 23 emit the laser beams 83 outwardly from the apparatus 100 such that one of the laser beams 83 is co-linear with the first axis 101, and such that the other laser beam 83 is co-linear with the second axis 22. Lasers 23 are preferably low-power lasers so that they do not pose a health risk.

Apparatus 100 also includes a hollow disc-shaped housing 51 which is approximately 50 mm in diameter and which includes an inner circular part 102 which one of the lasers 23 is fixed relative to, and an outer circular part 103 which the other laser 23 is fixed relative to. The outer part 103 is able to rotate relative to the inner part 102 in either a clockwise or an anticlockwise direction as indicated by the arrow 'A' in FIG. 13. The laser 23 which is fixed relative to the inner part 102 is the laser 23 which is for aligning the first axis 101 with first anatomical landmarks of the body, and the laser 23 which is fixed relative to the outer part 103 is the laser 23 which is for aligning the second axis 22 with second anatomical landmarks of the body. The angle between the lasers 23 and, hence, the axes 22 and 101 can be varied by rotating the outer part 103 relative to the inner part 102. The outer part 103 can be rotated relative to the inner part through 360 degrees.

A sensing means 30 of the apparatus 100 is able to sense an orientation of the second axis 22 relative to the first axis 101. In particular, sensing means 30 is able to determine the angular orientation of the second axis 22 relative to the first axis 101.

The sensed orientation is able to be output by the sensing means 30 to a processing means 40 which is in the form of a microprocessor 40. Microprocessor 40 is able to determine the angle between the first axis 101 and the second axis 22 by processing the sensed orientation which is output by the sensing means 30 in accordance with computer-readable instructions which are able to be read by the microprocessor 40 and which are stored on storage means which is in the form of a non-volatile memory 41. Microprocessor 40 is able to output the determined angle to a liquid-crystal display (LCD) 42 which is then able to display the angle numerically in units of degrees. The angle is displayed to the nearest degree. LCD 42 can display a maximum angle of 360 degrees and a minimum angle of 0 degrees.

A pushbutton switch 43 enables a user to control the operation of the microprocessor 40 and, hence, the apparatus 100.

Apparatus 100 is powered by a battery 44. The battery 44 may for example be a long-life lithium battery. The battery 44 can be charged by a battery charger such as a Universal Serial Bus (USB) charger 45 which is connected to an external charging supply of electricity 46.

Lasers 23, sensing means 30, microprocessor 40, non-volatile memory 41, LCD 42, and switch 43 are all housed within the housing 51. Housing 51 includes an opening or window 52 through which the measured angle which is displayed by LCD 42 can be viewed. It also includes a button 53 which is located on the front of the housing 51 adjacent to the LCD 42. Button 53 operatively engages with the switch 43 of the apparatus 100 such that the switch 43 is able to be operated by pressing the button 53. Although, for clarity, the lasers 23 are shown protruding from the housing 51, they may alternatively be located in the housing 51 such that they do not protrude from the housing 51 and such that the housing 51 does not obstruct the laser beams 83 which are emitted by the lasers 23.

Figure 13B:
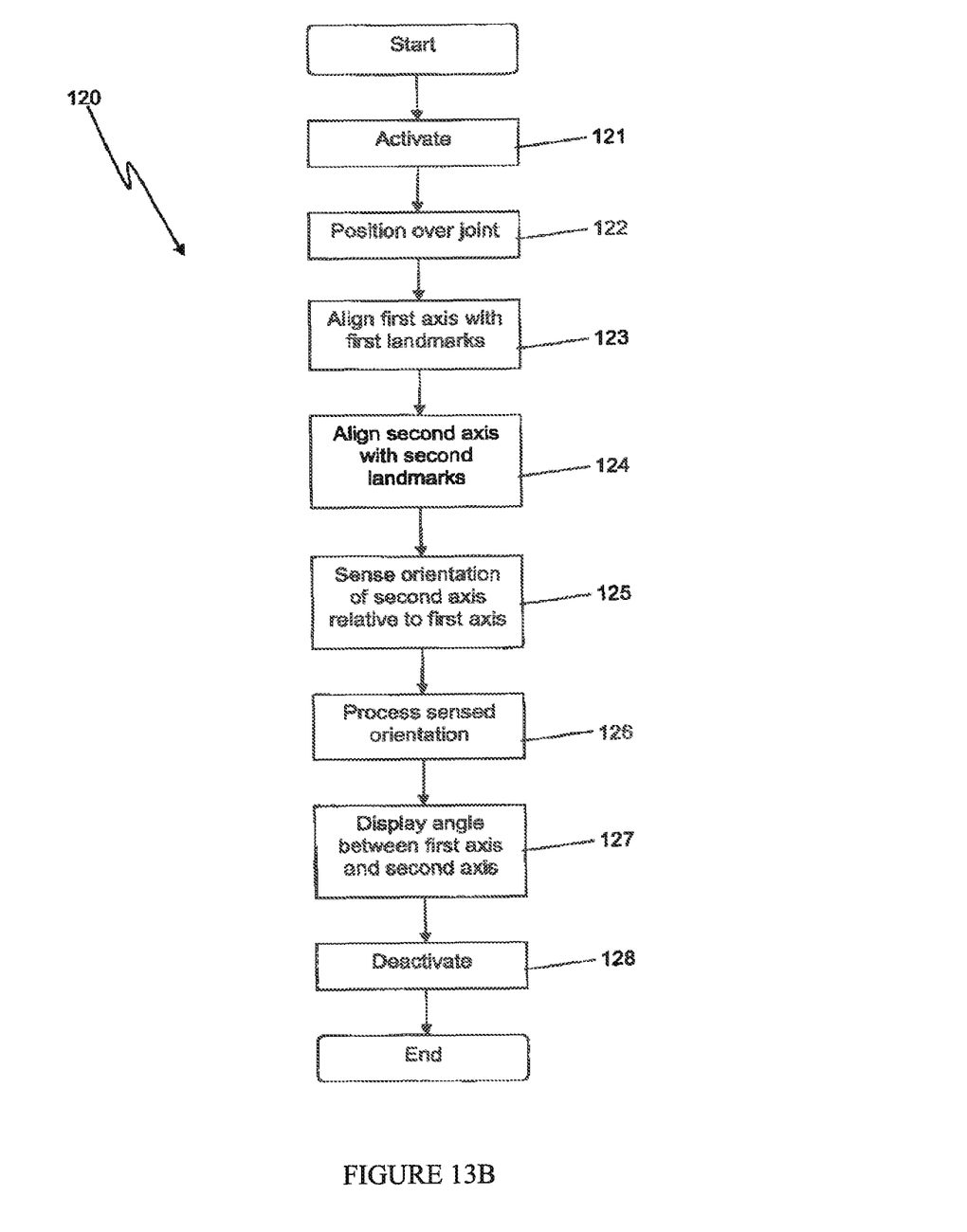
FIG. 13B is a flowchart of a method of operating the apparatus illustrated in FIGS. 12 and 13.

With reference to FIGS. 12 and 13, and also FIG. 14 which depicts a flowchart of a method 120 of operating the apparatus 100, the apparatus 100 may be used to measure an anatomical angle of a body joint by firstly performing an activation step 121. The activation step 121 involves a user pressing the button 53 to activate (i.e. turn on) the apparatus 100. Once the button 53 has been pressed, the lasers 23 emit laser beams 83, and the LCD 42 displays a numeric value in the range of 0-360 degrees. The value which is displayed by the LCD 42 depends on the orientation of the axis 22 relative to the axis 101 at the time, and will change dynamically if the orientation of the axis 22 relative to the axis 101 is altered by rotating the outer part 103 of the housing 51 relative to the inner part 102 of the housing. Rotating the outer part 103 relative to the inner part 102 changes the orientation of the axis 22 relative to the axis 101 by changing the angle between the axes 22, 101.

The next step of the method 120 is step 122 which is to position the housing 51 over the joint so that the laser beams 83 can be aligned with predetermined anatomical landmarks which are located above and below the joint.

At step 123 the laser beam 83 which is co-linear with the first axis 101 is aligned with first anatomical landmarks. The laser beam 83 is aligned with the first anatomical landmarks such that the laser beam 83 intersects each one of the first anatomical landmarks.

At step 124, the laser beam 83 which is co-linear with the second axis 22 is aligned with second anatomical landmarks. The laser beam 83 is aligned with the second anatomical landmarks such that the laser beam 83 intersects each one of the second anatomical landmarks.

Aligning the laser beams 83 with the first and second anatomical landmarks may require adjustment of the angle between the axes 22, 101 by suitably rotating the outer part 103 of the housing 51 relative to the inner part 102 of the housing 51.

At step 125, the sensing means 30 senses the orientation of the second axis 22 relative to the first axis 101 while those axes 22, 101 are aligned with the second and first anatomical landmarks, respectively. At step 126, the microprocessor 40 processes the sensed orientation to determine the angle between the first axis 101 and the second axis 22 and controls the LCD 42 to display the angle between the first axis 101 and the second axis 22.

At step 128, the apparatus 100 is deactivated (i.e. turned off) by pressing the button 53.

By employing lasers 23 instead of arms or the like as aligning means assists to make the apparatus described above more compact compared to existing goniometers which have long arms for alignment purposes.

The various apparatus described above may be used to measure the range of motion of an anatomical joint.

A user may operate the various apparatus described above using only one of their hands. This enables the user to use their free hand to assist a patient if need be, or to record the angular measurement which is obtained using the apparatus.

The lasers 23 allow the various axes of the apparatus described above to be accurately aligned with anatomical landmarks. This together with the automatic and accurate sensing, processing and display of the orientation of the various axes enables the apparatus to provide an accurate angular measurement which is more likely to be replicated between multiple measurements by the same user or measurements by different users. Consequently, the apparatus has an improved inter rater/therapist reliability and improved intra rater/therapist reliability compared to prior art devices.

In addition to being able to take accurate measurements which can be repeated by the same or different users, the apparatus are fast and easy to use.

The apparatus are able to measure anatomical angles irrespective of the orientation of the angle which is to be measured. Thus, it does not matter whether the angle to be measured lies in a horizontal plane, a vertical plane, or something in between. Consequently, the apparatus are able to be used to measure an anatomical angle of a person irrespective of the position of the person or the part of their body being measured.

The LCDs of the apparatus are sufficiently large to clearly display the angular measurement which is obtained using the apparatus.

The buttons 53 may be used to scroll through and select items from a menu which may be displayed by the LCD 42. The menu items may relate to configuring or selecting functions that the apparatus is able to perform. For example, the buttons 53 may be used to put the apparatus in to a normal measuring mode where laser beams 83 are emitted by both lasers 23, the small joint mode discussed earlier, or to select a landmark revision function. The LCD 42 may display instructions for to assist in operating the apparatus.

The housing 51 of the apparatus is preferably made from a material such as polycarbonate and aluminium for comfort and migration to the user, as well as for aesthetics and durability of the apparatus.

The battery charger 45 is not limited to being a USB battery charger and may be any sort of battery charger.

The display 42 may be a touch screen which can be used by a user to operate the apparatus. For example, the touch screen may display various options related to the operation of the apparatus, and the user may select any of those options by appropriately touching the touch screen.

It will be appreciated by those skilled in the art that variations and modifications to the invention described herein will be apparent without departing from the spirit and scope thereof. The variations and modifications as would be apparent to persons skilled in the art are deemed to fall within the broad scope and ambit of the invention as herein set forth.

Throughout the specification and claims, unless the context requires otherwise, the word "comprise" or variations such as "comprises" or "comprising", will be understood to imply the inclusion of a stated integer or group of integers but not the exclusion of any other integer or group of integers.

Throughout the specification and claims, unless the context requires otherwise, the term "substantially" or "about" will be understood to not be limited to the value for the range qualified by the terms.

It will be clearly understood that, if a prior art publication is referred to herein, that reference does not constitute an admission that the publication forms part of the common general knowledge in the art in Australia or in any other country.

The invention claimed is:

1. A handheld goniometer for measurement of anatomical angles of a body, comprising:
a housing having lasers secured therein for projecting at least one laser beam outwardly of the housing in alignment with an axis thereof, the housing positionable by a user in a first position to align the at least one laser beam with a first pair of anatomical landmarks and subsequently in a second position to align the at least one laser beam with a second pair of anatomical landmarks;
sensors, a user input device, a microprocessor and memory mounted in the housing for capture and storage of data on orientation in three dimensions of the housing when the user input device is operated; and
a digital display controlled by the microprocessor,
and wherein:
the microprocessor upon operation of the user input device in the first position causes capture in the memory of data on first orientations in three dimensions of the housing and axis, and upon a subsequent operation of the user input device in the second position causes capture of data on second orientations in three dimensions of the housing and axis, derives from the first and second orientations an anatomical angle between the first and second orientations of the axis, and displays the angle on the display, and the user input device comprises first and second switches with pushbuttons on opposite sides of the housing operable by a user pushing the pushbuttons towards each other.

2. The handheld goniometer of claim 1, wherein the microprocessor derives vectors representing the first and second orientations of the axis, transposes the vectors to a single plane and determines the anatomical angle as the angle between the two vectors in the plane.

3. The handheld goniometer of claim 2 wherein the plane is a horizontal plane.

4. The handheld goniometer of claim 1, wherein the sensors comprise a tilt sensor fixed within the housing and adapted to produce outputs from which a tilt angle of the axis relative to a horizontal plane and a roll angle of the housing about the axis are derived.

5. The handheld goniometer of claim 4, wherein the tilt sensor comprises a multi-axis accelerometer.

6. The handheld goniometer of claim 4, wherein the sensors further comprise a magnetometer secured in the housing and adapted to produce outputs from which a yaw angle about a vertical axis is derived.

7. The handheld goniometer of claim 1, wherein the lasers comprise first and second lasers that project laser beams in opposite directions outwardly from the housing.

8. The handheld goniometer of claim 1, wherein the handheld goniometer has a disc shape with a diameter and the axis extends along the diameter.

9. The handheld goniometer of claim 1, wherein the handheld goniometer has a disc shape with a diameter, wherein the axis extends along said diameter and wherein the pushbuttons have contours that comprise portions of the disc shape.

10. The handheld goniometer of claim 1, wherein the pushbuttons in use move on a line perpendicular to the axis.

11. The handheld goniometer of claim 8, wherein the housing is sized to be held by one hand of a user.

12. The handheld goniometer of claim 8, wherein the disc shape has a diameter of about 50 mm.

13. A method for measurement of an anatomical angle of a body, comprising the steps of:
holding a handheld goniometer in a first position wherein an axis of the handheld goniometer is aligned with a first pair of anatomical landmarks;
operating a user input device of the goniometer to cause sensing of data on a first orientation in three dimensions of the goniometer and the axis in the first position and storing said data;
subsequently holding the goniometer in a second position wherein the axis is aligned with a second pair of anatomical landmarks;
operating the user input device to cause sensing of data on a second orientation in three dimensions of the goniometer and the axis in the second position, and the user input device comprises first and second switches with pushbuttons on opposite sides of the handheld goniometer operable by pushing the pushbuttons towards each other; and
deriving from the data on the first and second orientations of the goniometer and its axis an angle between the axis in its first orientation and the axis in its second orientation, being an anatomical angle between the first and second pairs of anatomical landmarks.

14. The method of claim 13, wherein the handheld goniometer comprises a housing with lasers secured therein for projecting at least one laser beam aligned with the axis and wherein the at least one laser beam is aligned with the first pair of anatomical landmarks and subsequently with a second pair of anatomical landmarks.

15. The method of claim 14, wherein the lasers comprise first and second lasers which project laser beams in opposite directions so that the handheld goniometer can be positioned between members of the first pair of anatomical landmarks for capture of data on the first orientations of the housing and axis.

16. The method of claim 13, wherein the step of deriving the anatomical angle includes deriving vectors representing the directions of the axis in the first and second orientations, transposing the vectors to a single plane and determining the anatomical angle as the angle between the vectors in said plane.

17. The method of claim 16, wherein said plane is a horizontal plane.

18. The method of claim 13, wherein the handheld goniometer is held in one hand of a user during alignment of the axis with the first and second pairs of anatomical landmarks.

* * * * *